(12) United States Patent
Rickards

(10) Patent No.: US 9,056,113 B2
(45) Date of Patent: Jun. 16, 2015

(54) STEEPED HERBAL ANTI-BACTERIAL BODY WATER FOR CONSUMPTION AND TOPICAL USE—THE THYME LAVENDER OREGANO MINT NEEM SOLUTION FOR ACNE, EYELASH AND PORE CLEANSING, WRINKLES, BODY ODORS, BREATH FRESHENING, VAGINAL DOUCHING, TOENAIL FUNGUS, BLEPHRITIS

(71) Applicant: Peter Rickards, Twin Falls, ID (US)

(72) Inventor: Peter Rickards, Twin Falls, ID (US)

(73) Assignee: Peter Rickards, Twin Falls, ID (US)

( * ) Notice: Subject to any disclaimer, the term of this patent is extended or adjusted under 35 U.S.C. 154(b) by 0 days.

(21) Appl. No.: 14/019,473

(22) Filed: Nov. 8, 2013

(65) Prior Publication Data

US 2015/0132234 A1  May 14, 2015

(51) Int. Cl.
*A61K 8/02* (2006.01)
*A61K 36/534* (2006.01)
*A61K 36/53* (2006.01)
*A61K 8/97* (2006.01)
*A61Q 11/00* (2006.01)
*A61Q 15/00* (2006.01)
*A61Q 19/08* (2006.01)

(52) U.S. Cl.
CPC ............... *A61K 36/534* (2013.01); *A61K 36/53* (2013.01); *A61K 8/97* (2013.01); *A61Q 11/00* (2013.01); *A61Q 15/00* (2013.01); *A61Q 19/08* (2013.01)

(58) Field of Classification Search
CPC ....... A61K 36/534; A61K 36/53; A61K 8/97; A61Q 11/00; A61Q 15/00; A61Q 19/08
See application file for complete search history.

(56) References Cited

U.S. PATENT DOCUMENTS

2010/0233128 A1* 9/2010 Panasenko ................... 424/93.4

OTHER PUBLICATIONS

Ailment and Neem, Neem and its uses, Web archve Oct. 12, 2012, Retrieved from URL:<https://web.archive.org/web/20121026004209/http://www.neemwell.com/conditions_page2.htm>.*
http://adrianaevans.hubpages.com/hub/Goopy-eyes-home treatment (2014).*
http://www.mommypotamus.com/natural-remedies-pink-eye-styes (2014).*
http://www.oil-testimonials.com/essential-oils/9249/sticky-eye-mucus-brought-on-by-an-allergy (2014).*

* cited by examiner

*Primary Examiner* — Frederick Krass
*Assistant Examiner* — Nannette Holloman

(57) ABSTRACT

This innovation is a unique, natural, CONSUMABLE and topical treatment for many of my body's ailments that has helped me in ways other products never did. The anti-bacterial herbs appear to fight the root cause of the many ailments listed, instead of just masking them.
It cleansed my pores for acne. I sprayed it in and on my eyes. It gently allowed sebaceous debris, often called eye mucous, to painlessly ooze away from eyelash pores and other eye glands like NO other product I have heard of. It unclogged the micro eyelid circulation, greatly reducing the puffiness we all get with age. Cleaning pores allowed skin to heal itself better, reducing wrinkles and acne scars.
It naturally kills bacteria that cause odors under your arms and orally. It is consumable, so it works safely all the way down the back of the tongue where scrappers and chemical washes can't reach.

1 Claim, No Drawings

STEEPED HERBAL ANTI-BACTERIAL BODY WATER FOR CONSUMPTION AND TOPICAL USE—THE THYME LAVENDER OREGANO MINT NEEM SOLUTION FOR ACNE, EYELASH AND PORE CLEANSING, WRINKLES, BODY ODORS, BREATH FRESHENING, VAGINAL DOUCHING, TOENAIL FUNGUS, BLEPHRITIS

My Provisional Patent No. is 61/696,912 and this is the explanation of my product for my non-provisional patent application please.

This innovation is a unique, natural, CONSUMABLE and topical treatment for many of my body's ailments that has helped me in ways other products never did. The anti-bacterial herbs appear to fight the root cause of the many ailments listed, instead of just masking them.

It not only cleansed my pores for acne, but I used it both in and on my eyes, using a spray, although an eyedropper form would work, too. It gently allowed sebaceous debris, often called eye mucous, to painlessly ooze away from eyelash pores and other eye glands like NO other product I have heard of. It appears to unclog the micro eyelid circulation greatly reducing the puffiness we all get with age. It appears to cleanse pores, allowing the skin circulation to improve, healing itself better, reducing wrinkles and even my acne scars.

By naturally killing bacteria that cause odors under your arms and orally, it has greatly improved my body odors. Because it is consumable, it works safely all the way down the back of the tongue where scrappers and chemical washes can't reach.

At present, the formula is to steep one and a half tablespoons of each herb in one cup of water, like making tea. That can be dabbed on, but I filter it into a hand pumped spray bottle for easy quick full body application.

I love that any citizen can grow their own herbs, or buy them separately to make their own brew. I am freely spreading the good word, hoping good people can use this to help themselves heal, like I am doing.

However, I hope this patent will allow me the fun and financial right of any commercially sold products for these uses. Many people don't have the time to grow or brew their own and would enjoy purchasing the product in ready to use form. I hope to protect this innovation with a wide net for commercial promotion, including teabags, etc, as well as the ready-to-use product.

I hope that wide net allows that in the future, adjustments to the dose, adding or subtracting herbs, would be protected. That hopefully includes the use of diluting the more concentrated essential oils of these herbs, although right now the natural steeping action seems to make it safe and enough to use in my eyes, multiple times a day for a year now. I tried diluted mint oil on my skin and it stung, so probably the steeping will remain the best method, especially for the eyes.

The invention claimed is:
1. A method for drainage of eyelash comedones in a patient in need thereof, comprising:
i) steeping about one and one half tablespoons of thyme, lavender, oregano, mint and neem in about one cup of hot water to produce a solution; and ii) topically administering the solution, by eyedropper or as a spray, to the eye of said patient; wherein said administration causes eyelash comedone drainage.

\* \* \* \* \*